United States Patent [19]

Coughlin et al.

[11] Patent Number: 5,277,821

[45] Date of Patent: Jan. 11, 1994

[54] PURIFICATION OF SAMPLES BY INTERPHASE MASS TRANSFER USING MICROPOROUS HOLLOW-FIBER MEMBRANES

[75] Inventors: Robert W. Coughlin, Storrs; Edward M. Davis, Cheshire; Pramod Z. Rao, New Haven, all of Conn.

[73] Assignee: SymBiotech Incorporated, Wallingford, Conn.

[21] Appl. No.: 747,655

[22] Filed: Aug. 19, 1991

Related U.S. Application Data

[63] Continuation-in-part of Ser. No. 411,683, Sep. 25, 1989, Pat No 5,252,220.

[51] Int. Cl.$^5$ ............................................. B01D 63/02
[52] U.S. Cl. ................................ 210/644; 210/321.68; 210/500.23
[58] Field of Search ............... 210/634, 638, 644, 649, 210/321.65, 321.63, 321.68, 321.67, 500.23, 85, 637; 55/158; 435/315

[56] References Cited

U.S. PATENT DOCUMENTS

| | | | |
|---|---|---|---|
| 3,956,112 | 5/1976 | Lee et al. | 210/500.23 X |
| 4,516,580 | 5/1985 | Polanyi | 55/158 X |
| 4,517,080 | 5/1985 | DeLoach et al. | 210/34.63 X |
| 4,976,867 | 12/1990 | Callahan et al. | 210/637 |

Primary Examiner—Frank Spear

[57] ABSTRACT

Method and apparatus are provided for accomplishing improved separation and purification of an analyte by mass transfer between immiscible phases employing microporous hollow-fiber membranes. The invention eliminates several problems of the prior art. A number of possible modes of separation by mass transfer are possible according to the invention, including liquid-liquid extraction, back extraction, simultaneous forward and back extraction, gas absorption into a liquid, gas stripping from a liquid and simultaneous gas absorption and stripping.

22 Claims, 1 Drawing Sheet

PURIFICATION OF SAMPLES BY INTERPHASE MASS TRANSFER USING MICROPOROUS HOLLOW-FIBER MEMBRANES

This application is a continuation-in-part of an earlier application Ser. No. 07/411,683 filed in the USPTO on Sep. 25, 1989 now Pat. No. 5,252,220.

BACKGROUND OF THE INVENTION

The present invention provides method and apparatus for accomplishing mass transfer of a dissolved component from a first fluid phase to another, second fluid phase immiscible with the first phase (e.g. by liquid-liquid extraction or gas absorption) using microporous hollow-fiber membranes. This invention is especially useful for the purpose of preparation of analytical samples for subsequent assay by instrumental methods, including methods employing antibodies or antigens.. It has been found that the present invention provides improved and more convenient analytical sample preparation by mass transfer purification (e.g. liquid extraction or gas absorption) of an analyte and overcomes a number of problems of the prior art. The invention, although generally applicable to using mass transfer between fluid phases for analytical sample preparation, will be described mainly in terms of liquid-liquid extraction.

Liquid-liquid extraction (herein sometimes referred to as LLE) is a general and widely used method of preparing samples for later assay by liquid chromatography, gas chromatography, spectrophotometry and other analytical instrumental methods. LLE is particularly useful when the compound to be assayed is lipophilic as in the case of a fat soluble drug. In such a case, the solute (i.e. the drug) would be extracted from the analyte (e.g., a serum or urine sample) into a liquid solvent (often an organic or hydrocarbon solvent). It could then be back-extracted (or stripped) from the solvent into another liquid, often aqueous and referred to herein as the stripping phase, the product liquid or the product phase. LLE helps to free the soute (e.g. a drug) from interfering substances and can concentrate the solute as well. During forward extraction LLE will tend to concentrate a solute compound in an organic solvent liquid, if the compound is more soluble in the organic solvent liquid than in an aqueous analyte sample. The equilibrium condition of two immiscible phases in contact is often expressed in terms of a distribution coefficient, D, herein defined as:

$$D = \text{(equilibrium concentration of solute in organic solvent phase)/(equilibrium concentration of solute in aqueous phase)} \quad (1)$$

A value of D greater than unity states that the organic phase is favored over the aqueous phase by the solute of interest. A "forward" extraction of a solute from an aqueous feed liquid phase to an organic solvent liquid phase is favored by a distribution coefficient greater than unity as defined by the foregoing equation (1). Back extraction or stripping of a compound from organic solvent liquid to aqueous stripping liquid is favored by a distribution coefficient smaller than unity as defined by the foregoing equation. It is often possible to adjust the distribution coefficient to a favorable value by choosing suitable conditions of pH, temperature and other conditions.

For ease of notation and uniformity, the analyte or liquid sample-to-be-analyzed will often be referred to herein as the feed, feed liquid, feed sample or feed phase, the solvent as solvent liquid or solvent phase (the solvent liquid will often be a hydrocarbon or organic solvent, including organic solvents containing reverse micelles) and the stripping liquid as product, product phase, product liquid or stripping phase. The use of LLE for preparation of analytical samples is further discussed in the following references: D. N. Bailey and M. Kleiner, J. Anal. Toxicology, 8, 26 (1984): E. H. Forester and M. F. Mason, J. Foren. Sci, 19, 155 (1974); I. Sunshine (ed), *Handbook of Analytical Toxicology*, CRC Press, Cleveland (1969).

In addition to being a traditional method of analytical sample preparation, LLE is also a unit operation of chemical engineering used for stage-wise and continuous operations on a larger scale. The smaller-scale use of LLE for analytical sample preparation is generally a batch process, whereas the traditional use of LLE as a larger-scale unit operation is generally a continuous-flow operation. The latter use of LLE is described generally in McCabe, W. L. and Smith, J. C., Unit Operations of Chemical Engineering, 3rd Ed., McGraw-Hill, N.Y., 1976, pp. 465-800.

Traditional LLE applied to analytical sample preparation requires the handling of several different liquids, is labor intensive requiring considerable manual manipulation, employs considerable volumes of solvents that are often toxic and suffers from problems such as formation of emulsions which are slow and difficult to separate. For such reasons a new approach has gained favor in recent years in which an organic solvent phase is bonded to a solid support such as silica. This modern innovation is often called solid phase extraction or SPE. SPE is described further by the following references: Tibbins, B.: Nature, 334, pp. 273-274, 21 Jul. 1988; Amer. Biotech. Lab, 5, (1), pp. 25-31 (1987); Amer. Labor News, p. 8, June, 1987; Majors, R. E., LC-GC, 4 (10), pp. 972-9844 (1986); McDowell, R. D., et al: J. Pharm. Biomed. Anal., 4 (1), pp. 3-21 (1986).

SUMMARY OF THE INVENTION

The present invention provides improved analytical sample preparation by mass transfer from one immiscible phase to another by employing microporous hollow fiber membranes to manage and control the interface between immiscible phases. An important case is the use of LLE for sample preparation by transfering an analyte from one immiscible liquid to another using microporous hollow fiber membranes. This approach overcomes some of the problems of traditional LLE mentioned supra, and avoids many problems of SPE such as: lack of flexibility in choosing the SPE solvent phase from only those bonded phases available commercially, requirements of large volumes of solvent to condition the SPE solid phase, and solid waste disposal of the spent SPE solid phase after use. The application of microporous hollow fiber membranes (hereinafter sometimes referred to as MPHFM's) to LLE has been earlier disclosed by Cussler, E. L., et al in European Patent Application No. 87304204.8 (European Patent Office Publication No. 0246065; A1). Kiani, A., et al, Journal of Membrane Science, 20, pp. 125-145 (1984) disclose an LLE process employing a planar microporous hydrophobic membrane having an immobilized liquid-liquid interface. However, each of the latter disclosures have been concerned mainly with LLE by continuous flow processes on a large scale. Surprisingly, we have discovered that performing LLE by microporous hollow fibers on a smaller scale batch operation suitable for analytical sample preparation can entail choices regarding novel methods and modes of operation and novel device aspects, as we disclose hereinbelow. We also disclose improved method and apparatus for LLE.

Liquid-liquid extraction processes typically involve a liquid feed containing a solute and an immiscible liquid extractant solvent. Mass transfer of the solute can occur at an interface between the two immiscible phases. It is typical in these processes to attempt to increase their efficiency for mass transfer by maximizing the interfacial surface area between the two phases. Traditionally, LLE processes have been carried out in devices such as packed towers, mixer-settlers, etc., which seek to optimize this interfacial surface area. The intimate mixing that often occurs in these devices often, however, leads to the formation of stable emulsions of the two phases, thereby inhibiting phase separation and product recovery. Traditional LLE systems have avoided using liquids having similar densities, a situation which appears to promote this problem of emulsion formation.

The present invention uses a microporous membrane to establish a support for interfacial contact between two immiscible phases, e.g. two immiscible liquids in the case of LLE. When such a microporous membrane is wet with a liquid fluid, the fluid fills the pores of the membrane. If a second immiscible liquid is then allowed to contact the membrane on one side of the membrane, an interfacial contact area is established on that side of the membrane at its surface. This interface is stabilized at the membrane surface by maintaining a higher pressure on the non-wetting liquid than on the wetting liquid, but with said pressure on the non-wetting liquid lower than that necessary for the non-wetting liquid to displace significantly the wetting liquid from the pores of the membrane. (This stabilization requirement has been discussed by Kiani, et al and can also result in the liquid-liquid interface being established within the pores of the membrane.) The problems discussed above for traditional liquid-liquid extraction systems can be avoided when the liquid-liquid extraction interface is established at the surface of the microporous membrane, or within its pores, in the LLE process described herein.

The use of MPHFMs for preparing analytical samples for assay, (e.g. by spectrophotometry, fluorimetry, fluorescence, high performance liquid chromatography, gas chromatography, refractometry) avoids or eliminates many problems of the prior art by: (1) permitting very small sample volumes to be employed and manipulated, e.g. a few microliters; (2) permitting the use of very small volumes of other phases, e.g. of toxic organic solvents in the case of LLE; (3) avoiding the formation of persistent, troublesome dispersions of one phase in another, e.g. emulsions in the case of LLE; (4) avoiding interferences from filterable particles which are retained in the sample phase by the MPHFM and thus do not enter a receiving phase (such as a solvent or stripping solution in the case of LLE) where they can interfere with instrumental assay, as by spectrophotometry. For example, the use of a MPHFM having suitable pore size can permit the extraction of an analyte from whole blood into a clear receiving phase while retaining red blood cells (RBCs) in the sample; the use of the MPHFM then avoids interferences by the RBCs in subsequent assay by an instrument and eliminates the need to centrifuge the blood before assay as is ordinarily the practice in the prior art.

The solute extracted by the present invention can comprise virtually any species which is soluble in both the feed and the extractant solvent. Both organic and inorganic species can be separated by means of the present invention. Further, polymeric species, especially proteins, having a diameter of less than about the membrane pore size, can be separated by the present process. Still further, multiple solute species can be separated by the present invention. Preferred solutes comprise biological compounds, such as, but not limited to, polypeptides and proteins, and bio-affecting compounds, such as, but not limited to, drugs, pharmaceuticals, enzymes, vitamins, and hormones. Still further, the present invention can be used to extract other inorganic and organic species, including pesticides, chlorinated organic compounds, fuels, petrochemicals, metal ions and metal complexes and mixtures thereof.

Preferred MPHFM materials include polyolefins, cellulose esters polymers, polyamides, polyacrylamides, poly(sulfonated styrene), glass, polysulfones, and polyacrylics. Most preferred are cellulose acetate polymers, polyethylene, polypropylene, polymethylpentene, and polytetrafluoroethylene.

Preferred microporous membrane structures include a microporous membrane having a thickness of 1 to 75 microns, an average pore size of 50 to 100,000 angstroms, and a porosity of from less than 1% up to about 99%. Generally, the pores are sufficiently large to admit a liquid that wets the material, but sufficiently small to prevent the flow therethrough of non-wetting liquids under moderate pressure driving forces up to several atmospheres. In the case of microporous hollow fiber membranes, it is preferred that such membranes have a wall thickness of 1–75 microns, an inner diameter of 3–1500 microns, an average pore size of 50–2000 angstroms, and porosity of from less than 1% up to about 99%. Celgard TM M microporous membranes, including Celgard X20 TM M microporous hollow fibers (which are commercially available from Celanese Separations Products, Charlotte, N.C.) can be employed in this invention, as can MPHFMs from a number of other manufacturers.

According to the present invention, sample preparation by LLE is made more convenient by employing microporous hollow fiber membranes in the form of a single fiber in a process and device. The invention permits either sequential or simultaneous contacting of immiscible liquid phases and provides for convenient mixing to increase mass transfer rates. The present invention avoids and eliminates poor distribution of fluids among several MPHFM fibers, a problem which has plagued the prior art. The invention also provides great flexibility regarding the choices of fluid volumes that can be used for interphase mass transfer and permits good control of fluid volume size, an important requirement for quantitative analysis of samples.

An object of the present invention is to provide improved process and apparatus for analytical sample preparation by interphase mass transfer, e.g. LLE, using microporous hollow fibers, that is convenient and has enhanced rates of mass transfer.

It is a further object that said process be operable in a sequential or simultaneous mode regarding the contacting of the fluid phases (feed phase, solvent phase and stripping or product phase in the case of LLE).

Yet another object is to provide for single-step mass transfer from one fluid phase to another, e.g. LLE from a feed liquid to a solvent liquid.

Still another object is to provide analytical sample preparation with simultaneous forward LLE and stripping of an analyte by the use of a solvent supported in the pores of MPHFM's.

Another object is to provide sample preparation by simultaneous gas absorption and stripping of an analyte by the use of a gas phase within the pores of a MPHFM.

It is yet another object to provide an apparatus for convenient LLE of samples using microporous hollow fibers that provides enhanced mass transfer rates.

Another object is to provide apparatus which can be used to accomplish LLE conducted according to several different modes of operation.

Yet another object is to provide an apparatus and method which avoids and eliminates mal-distribution of fluid phases within multiple MPHFMs.

Still another object is to eliminate the need for multiple sealing of multiple MPHFM fibers thereby providing simple and low-cost manufacturing of mass transfer devices for sample preparation using MPHFMs.

Yet another object is to provide flexibility regarding the sizes of fluid volumes employed in mass transfer purification of analytical samples in a device that has convenient and compact dimensions.

The foregoing and additional objects will become apparent to one skilled in the art who examines the description of the invention disclosed herein.

BRIEF DESCRIPTION OF THE DRAWINGS

FIG. 2 of the parent application Ser. No. 07/411,683 depicts a flow diagram of a computer-program system for computing and outputting product-recovery ratios and product-concentration ratios of the various modes in which the apparatus and processes of the present invention can be operated, as well as for outputting rules for selecting optimum liquid volumes for use in the various possible modes of the present invention.

PROBLEMS OF THE PRIOR ART

Unexpectedly, we have discovered an especially advantageous and useful MPHFM apparatus for interphase mass transfer purification (e.g. liquid-liquid extraction) of batch analytical samples that employs a single-fiber MPHFM and simultaneously solves several problems in this art. These problems include the following:

Problem 1. Accommodating Fluid Volumes of Different Size

It is desirable that an extraction apparatus be able to handle feed sample volumes and receiving-liquid volumes of different size. The term receiving liquid indicates a liquid into which an analyte is transferred and is meant to include either a stripping liquid or a solvent liquid which is immiscible with both feed-sample liquid and stripping liquid. For example, when the feed sample is blood plasma, it may be necessary to work with a very small sample volume (e.g. 50 microliters) as when the blood is drawn from an infant. When the sample volume is small, then it will also often be desirable that the receiving liquid (e.g. an extraction solvent or a stripping solution) also be similarly small in volume to avoid diluting the analyte. However, in some other cases it may be desirable that the receiving liquid be of large volume (e.g., several ml) in order to recover a large amount of analyte (which can be later concentrated in the receiving liquid by subsequent evaporation). In other cases, the feed sample may be dilute and contain only small amounts of analyte; if, in such cases, a large volume of feed sample is available, it will frequently be desirable to extract analyte from a relatively large volume (e.g., several ml) of feed sample into a relatively small volume (e.g., several microliters) of receiving liquid, so as to concentrate the analyte therein.

Thus, it is desirable to have an apparatus that can employ volumes of different size, for feed-sample liquid as well as for receiving liquid (extraction solvent or stripping solution). The latter statement is also true for an MPHFM apparatus used to accomplish mass transfer of an analyte by gas absorption or by gas stripping.

Problem 2. Non-Uniform Filling of MPHFMs

Prior art teaches the construction of MPHFM extraction devices by sealing MPHFMs of about equal length into a shell tube to form a module constructed similar to a shell-and-tube heat exchanger. In such a device, the intra-lumenal and extra-lumenal volumes (where feed liquid, solvent or stripping solution may be placed) can be adjusted by adjusting the length and number of MPHFMs and the length and diameter of the shell tube. Such prior art includes Lee et al. (U.S. Pat. No. 3,956,112), Dahuron and Cussler [(AlCHE Journal 34, 130 (1988)], Ding et al. [AICHE Journal 35, 814 (1989)] or D'Elia et al. [J. Membrane Science 29, 309 (1986)]. Similar prior art for the use of MPHFMs in gas absorption and gas stripping has been disclosed by: Qi and Cussler [J. Membrane Science 24, 43–57 (1985)], Semmens et al [J. Membrane Science 51, 127–140 (1990) and J. Amer. Water Works Assoc. 81(4), 162–167 (1989)], Yang and Cussler [J. Membrane Science 42, 271–280 (1989)].

When multiple, parallel MPHFM fibers are employed in a device to adjust the total lumen volume (to accommodate a desired volume of either a feed-sample liquid or a receiving liquid in the lumens), then problems are encountered in uniformly filling the parallel lumens. Due to minor random variations in shapes and sizes, the lumens of MPHFM fibers seldom fill uniformly when one attempts to place a liquid into several parallel MPHFM fibers simultaneously. This is a serious problem because it can interfere with analytical accuracy which requires knowing the volumes of the liquids undergoing extraction. Especially when only a small volume (e.g. infant blood) is available for assay it is difficult and frequently impossible to place the entire feed sample within parallel lumens of multiple MPHFM fibers; some of the feed sample can remain in dead space in the manifold upstream of the lumens; another portion of the feed sample can be forced through and out of the lumens of some of the MPHFM fibers which offer less resistance to flow when the other fibers offer more resistance to flow.

Problems of mal-distribution of fluid in multiple fibers of MPHFM devices are disclosed and discussed by Park and Chang [AIChE Journal 32, p. 1937 (1986)]. These problems and considerations apply to MPHFM devices used for LLE or for gas absorption or gas stripping.

Problem 3. Cost and Complexity of MPHFM Devices

Incorporating increasing numbers of MPHFM fibers in a device to increase the total lumen volume and the total extraction area is taught by the prior art as discussed under Problem 2 just above. However incorporating multiple MPHFM fibers increases the cost of manufacture and increases the number of seals required at the ends of the fibers, thereby increasing the probability of undesired leaks at the seals. Similar cost and complexity considerations apply to MPHFM apparatus used for LLE or for gas absorption or gas stripping.

Problem 4. Increasing Transfer Area and Decreasing Mean Transfer Distance

It is desirable to increase rates of mass transfer in liquid extraction using MPHFMs by increasing mass-transfer area, which is determined by MPHFM fiber wall area. Therefore, it is desirable to have large MPHFM fiber wall area per unit volume of fiber lumen and per unit of shell volume in order to achieve large mass transfer rates per unit volume of liquid within the fiber lumen and per unit volume of liquid within the shell. Because the ratio of wall area to volume of a cylinder is equal to 4/D (four divided by the fiber diameter), it will often be desirable to use very narrow-bore MPHFM fibers to obtain large fiber-wall area per unit lumen volume. Furthermore it is also often desirable to have a shell tube of small diameter in order to have large values of MPHFM wall area per unit volume of liquid in the shell tube. Rates of mass transfer are also improved by minimizing the length of the mean transfer distance; since mass transfer is essentially in the radial direction with MPHFMs, it is also important to minimize the radius of the MPHFMs and the radius of the shell tube in order to minimize the mean transfer distances.

Prior art, as referenced above, teaches the use of multiple, parallel MPHFMs of narrow diameter placed within a shell tube of sufficient diameter to accommodate the multiple MPHFM fibers but still small in order to minimize the mean mass transfer distance in the shell and the volume of the shell-side volume relative to the transfer area of the MPHFMs. Similar considerations of mass transfer area and distances apply to MPHFM devices used for LLE or for gas absorption or gas stripping.

Problem 5. Mixing Liquids During Liquid Extraction with MPHFMs

We have found that mixing the liquids, especially the liquid external to the MPHFMs during liquid extraction can significantly increase the rate of the extraction process. However constructing modules of multiple MPHFM fibers within a narrow shell, as taught by the prior art, leads to a device in which it is very difficult to mix the liquids during extraction, especially when the extraction is performed as a batch process, as is often the case with extraction to prepare samples for assay. Similar considerations of mixing fluid phases to enhance mass transfer apply to MPHFM devices applied to gas absorption or gas stripping as well as to LLE.

We have attempted to solve Problems 1 through 5 recited above by employing a single MPHFM fiber of adjustable length to accommodate different volumes within the single lumen. Because the volume of the lumen can be readily adjusted by adjusting its length, and because a known volume of liquid equal to or less than the lumen volume can be readily placed in the lumen, the resulting device can be used for quantitative analysis. However, if a single long, narrow MPHFM fiber is placed in a long, narrow, straight shell tube as suggested by prior art, and as required to maximize mass-transfer area and minimize mean mass-transfer distance, it becomes difficult to mix a liquid outside or inside the lumen. Even using relatively small lumen volumes, the required length of a desirably thin fiber can become too long to be accommodated in a straight-tube shell of compact dimensions.

A simple example illustrates some of the foregoing problems. Typical MPHFMs are available with inner diameters (i.d.) of about 400 micrometers. For a 400 micrometer i.d. MPHFM fiber, a length of 1 cm has a lumen volume of about 1.26 microliter. Thus, for a fiber of 400 microliters i.d., a length of fiber of about 40 cm, would be needed to hold a feed sample of about 50 microliters in the lumen. To build a compact device of largest dimension about 4–5 cm, and which employs about 40 cm of 400 micrometer i.d MPHFM fibers, the use of about 10 parallel fibers, each about 4 cm long, is suggested by prior art such as that cited earlier. If a single 40 cm long MPHFM fiber is to be employed, the prior art then suggests placing the single fiber in a long, straight narrow tube, thereby resulting in an unwieldy device longer than 40 cm. Moreover, it would be very difficult to achieve good mixing of a liquid in contact with the outer wall of the long MPHFM fiber within the narrow shell tube. With a long single MPHFM fiber in a long straight tube, the device would be too unwieldy and clumsy for convenient, routine laboratory use.

DETAILED DESCRIPTION OF THE INVENTION

Unexpectedly, we have solved all of the Problems 1 through 5 above by an apparatus that incorporates a single MPHFM fiber mounted on a support body such as a framework, a rod or a spindle. A framework can be of struts, latticework or wire, e.g. a cage. The supporting body can be constructed of any suitable material such as a plastic resin (e.g polyethylene, nylon or Teflon), wood, glass, vitreous or ceramic material or a metal. If the supporting body is a solid material, then it is preferred that the surface of the body in contact with the MPHFM fiber be interrupted or roughened to improve access of liquid to the outer surface of the MPHFM fiber in order to improve mass transfer. This type of surface is referred to herein as a "mass-transfer enhancing surface". Such a mass-transfer enhancing surface can be rugose, porous, channelled, ribbed, grooved, dimpled or imbricated.

The MPHFM fiber can be fixed to the supporting body by epoxy resin, another suitable cement or other mechanical means. The supporting body serves to fix the shape and dimensions of the device and prevent deformation or kinking of the MPHFM fibers which can block flow in the fibers. In a preferred embodiment with a fiber longer than a several centimeters, the MPHFM fiber is wound around the supporting body with at least a small distance between the windings so that external liquid can contact as much as possible of the outer wall of the fiber without interference from neighboring windings. The supporting body need not be cylindrical or even of round cross section, e.g. its cross section could be elliptical, oval or polygonal.

In a preferred embodiment, the apparatus also includes a container which holds a liquid; the supporting body (with the single MPHFM fiber mounted on it) fits inside the container so that the MPHFM is immersed at least partially in a liquid held in the container. In a preferred embodiment, both supporting body and container are of circular, cylindrical cross section. A preferred size range for the diameters and heights of supporting body and container is about 0.2 to 10 cm, with 1 to 5 cm being especially preferred. Preferred inner diameters of the MPHFM fibers are about 3 to 1500 micrometers, with about 50 to 1000 micrometers being especially preferred.

The rate of mass transfer can be increased during separation by interfacial mass transfer by agitating at least one of the liquids to cause mixing. During liquid extraction according to the present invention, either the supporting body or the container can be moved or rotated (one relative to the other) to cause mixing of the liquid held in the container. This permits convenient mixing of small volumes of liquid in the container; it is often difficult to mix small volumes of fluid. Mixing can also be caused by vertical motion of container and supporting body relative to each other, or by sparging gas through the liquid in the container, by a stirring bar within the container, by sonification, by vibration, by applying a Vortex mixer to the device or by many other mixing means known in the art. In some instances it may be desirable to place baffles in the container to improve mixing. Generally, mixing can occur in the liquids inside as well as outside the lumen and it is intended that at least one of these liquids be mixed to improve mass transfer. In a very useful embodiment, mixing can be achieved by holding the assembly of MPHFM fiber mounted on a supporting body within a flowing liquid such as a river or brook in order to take advantage of movement of water relative to the apparatus while extracting an analyte from the flowing water to a receiving liquid within the device; or a small assembly could be placed in a blood vessel in order to extract analyte from flowing blood into a receiving liquid in the device.

Description of a Preferred Embodiment of a Single-Fiber Apparatus

Figure 1:
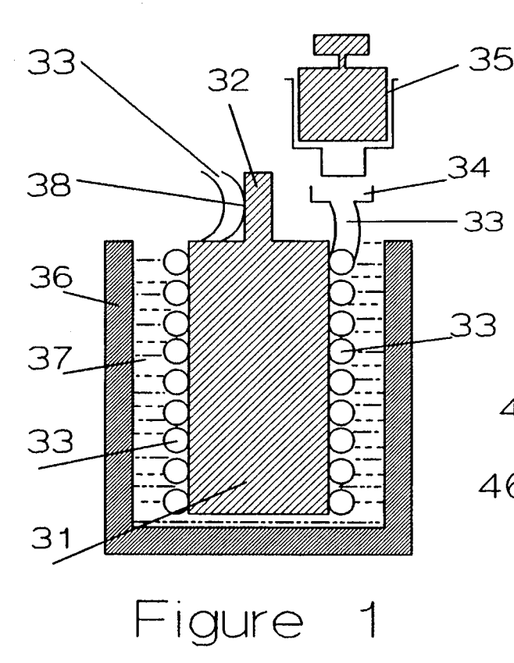
FIG. 1 depicts schematically a side-view cross-sectional diagram of an apparatus for liquid-liquid extraction with a single MPHFM fiber wound around a supporting body according to the present invention.

A single-fiber apparatus according to the instant invention is depicted in FIG. 1. As shown in FIG. 1, the apparatus includes a spindle 31 with an integral shaft 32 by which the spindle 31 can be rotated or held stationary. A MPHFM fiber 33 is wound around spindle 31 to form an assembly comprising MPHFM fiber 33 and spindle 31. The inlet end of MPHFM fiber 33 is sealed into a Luer fitting 34 into which a hypodermic syringe 35 can be inserted to fill the lumen of the hollow MPHFM fiber 33 with either a feed-sample liquid or a receiving liquid (e.g. a solvent or a stripping solution).

In a special preferred embodiment, the wall of a portion of the MPHFM fiber 33 adjacent the inlet end attached to fitting 34 is made non porous, for example by heat sintering or coating the fiber with an adhesive resin. The non-porous part of the MPHFM fiber 33 extends from inlet fitting 34 to a location below the surface of liquid 37 and serves to prevent air from entering or leaving the lumen of fiber 33 through pores in the fiber wall during insertion of a small volume of liquid into the lumen, or during removal of a small liquid volume from the lumen of fiber 33. The non-porous section of MPHFM fiber 33 is not indicated in FIG. 1. A short length of solid-walled tubing connected between the MPHFM fiber 33 and fitting 34 can be substituted for the non-porous section of fiber 33. The non-porous length of conduit between fitting 34 and the submerged portion of MPHFM fiber 33 permits a small bolus of liquid to be inserted into the porous part of fiber 33 by pressure as can be applied by syringe 35, or to be removed from said fiber 33 by vacuum as can also be applied by syringe 35.

The assembly comprising spindle 31 and MPHFM fiber 33 fits into container 36 which holds liquid 37. Liquid 37 can be either a feed-sample liquid or a receiving liquid. The other (non-inlet) end of the MPHFM fiber 33 is fixed to the spindle shaft 32 at position 38. It is desirable that both ends of the MPHFM fiber 33 protrude above the upper surface of liquid 37 in container 36; in the device of FIG. 1 the non-inlet end of the MPHFM fiber 33 is threaded through a passage (not shown) inside spindle 31 and emerges near shaft 32 where it is anchored by a bead of epoxy cement at position 38. The volume of liquid 37 will be determined by the relative volumes of container 36, spindle 31 and MPHFM fiber 33. For a particular size combination of spindle 31 and MPHFM fiber 33, the volume of liquid 37 can be adjusted or selected as desired simply by adjusting or selecting the volume of container 36.

Any convenient means of placing a liquid in the lumen of MPHFM fiber 33 (or removing liquid therefrom) can be employed, and the Luer fitting 34 and syringe 35 are depicted only for illustrative purposes. Furthermore any convenient means can be used to anchor the MPHFM fiber 33 to the spindle 31. Similarly any convenient means known in the art can be employed for placing liquid in container 36, or removing liquid therefrom. Similarly, there are many possible ways of winding the MPHFM fiber 33 on the spindle 31 and anchoring the MPHFM fiber 33 and its ends to the spindle 31 or spindle shaft 32.

Figure 2:
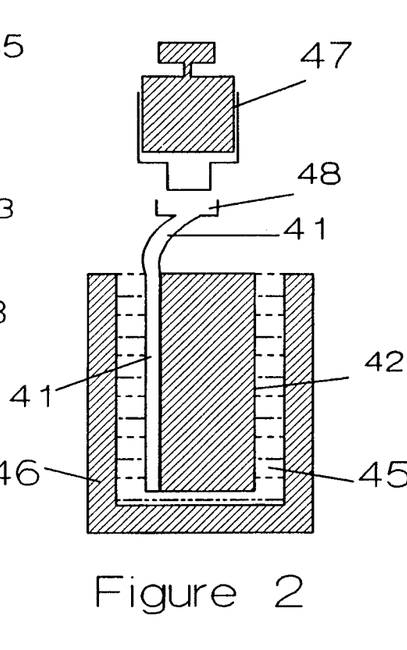
FIG. 2 depicts another similar apparatus with a single MPHFM fiber mounted on, but not wound around, a supporting body.

If the MPHFM fiber is sufficiently short then it need not be wound around the supporting body but need only be mounted thereon by a suitable means. In FIG. 2, the MPHFM fiber 41 is shown mounted on a supporting body 42 within liquid 45 in container 46. Container 46 can be made of a small piece of tubing closed at one end. Liquid is admitted to MPHFM fiber 41 from syringe 47 through fitting 48. Liquid is placed in container 46 by any suitable means and mixing of at least one of the liquids is accomplished as described above. A short length of MPHFM fiber could also be mounted on a thin needle and the resulting assembly inserted through a suitable catheter into a blood vessel in order to extract an analyte from the blood therein. Supporting body 42 can also be equipped with paddles or propellers to aid in mixing liquid 45, but this is not shown in FIG. 2.

Applications

The following Applications 1–5 illustrate a number of ways in which the single-fiber MPHFM device can be used for liquid extraction and/or stripping.

Application 1. Simultaneous Extraction and Stripping

To use the apparatus of FIG. 1 in the supported-solvent-membrane mode for simultaneous extraction and stripping, a feed sample is pumped into the MPHFM fiber 33 from the hypodermic syringe 35 via Luer fitting 34. The assembly comprising spindle 31 and MPHFM fiber 33 is then immersed briefly in a solvent that is immiscible with the feed sample and wets the wall of the MPHFM fiber 33 and fills the pores therein. Typically, most organic solvents will wet and fill the pores of a MPHFM made of polypropylene. Alternatively, the pores of the MPHFM can be filled with solvent that wets the MPHFM by placing a small amount of solvent in the lumen of the MPHFM fiber 33 before the feed sample is placed therein. The assembly comprising MPHFM fiber 33 and spindle 31 is then removed from the solvent, excess solvent allowed to drip off or evaporate and then the assembly is placed in a stripping liquid 37 held within container 36.

With fiber 33 mounted on spindle 31 placed in container 36, stripping liquid 37 is mixed or agitated in container 36 by rotating the spindle 31 and container 36 relative to each other, or by using another suitable mixing means known in the art such as those described earlier. During the course of extraction (the rate of extraction being enhanced by mixing in the present case), the analyte is transferred from feed solution in the lumen of MPHFM fiber 33, into the solvent in the pores of the wall of MPHFM fiber 33, then from said solvent in the pores into liquid 37. Thereafter, liquid 37 which now contains the analyte is recovered.

The apparatus can also be operated by placing a stripping solution in the lumen of MPHFM fiber 33, solvent in the pores of the wall of MPHFM fiber 33 as described above, and a feed sample in the container 36 to serve as liquid 37. In the latter case, analyte is transferred from the feed sample in container 36, to the solvent in the pores of MPHFM fiber 33, and then to stripping liquid 37 in the lumen of MPHFM fiber 33.

Application 2. Single-Step Extraction

The apparatus of FIG. 1 can also be used for single step extraction by pumping a feed sample from syringe 35 into the lumen of MPHFM fiber 33, then submerging the assembly comprising spindle 31 and MPHFM fiber 33 into an organic solvent liquid 37 that is immiscible with the feed sample and held in container 36. Liquid 37 in container 36 is now organic solvent in this Application. Said organic solvent liquid 37 wets the wall of MPHFM fiber 33 and fills its pores. Container 36 and spindle 31 are then moved or rotated with respect to each other to mix at least liquid 37 while analyte is transferred from feed sample in the lumen of MPHFM fiber 33 into solvent liquid 37. Single-step extraction can also be accomplished in the opposite direction, from a feed sample held in container 36 (now as liquid 37 in this Application) into an immiscible organic solvent in the lumen of MPHFM fiber 33.

Application 3. Single-Step Stripping

The apparatus of FIG. 1 can also be used for a single-step stripping of analyte from an organic solvent to an immiscible stripping solution. Solvent containing an analyte can be placed in the lumen of MPHFM fiber 33 and stripping solution in container 36 followed by mixing to increase the rate of mass transfer. Conversely, the locations of solvent and stripping solution can be reversed to achieve mass transfer in the opposite direction.

Application 4. Sequential Extraction and Stripping

Yet another possible mode of operation of the apparatus of FIG. 1 is to perform sequential extraction and stripping. For example, after a single-step extraction of analyte from feed sample held in container 36 into solvent in the lumen of MPHFM fiber 33, the assembly comprising spindle 31 and MPHFM fiber 33 which contains the solvent and extracted analyte, is removed from container 3 and then placed in another similar container which holds stripping solution in order to accomplish the stripping step. The latter step can also be accomplished by stripping solution placed in the original container 36 after it is washed and rinsed free of the feed sample. As before, the extraction and stripping in each of the sequential steps can be accelerated by mixing.

Conversely, using the same device, mass transfer can also be conducted in the direction opposite to that of the preceding paragraph. Thus analyte can be forward extracted (with acceleration by mixing if desired) from a feed sample in the lumen of MPHFM fiber 33 into solvent held in container 36, whereafter MPHFM fiber 33 and spindle 31 are withdrawn from the container 36. Then stripping (or back extraction) is performed by placing another, different assembly comprising spindle 31 plus MPHFM fiber 33 (which no contains stripping solution) into liquid 37 (now solvent liquid containing analyte in this Application) held in container 36 and again mixing to permit back extraction of analyte from the solvent liquid 37 in container 36 into the stripping solution in the lumen of MPHFM fiber 33. Alternatively, the original MPHFM fiber 33 could be cleaned, then stripping solution placed in its lumen, and then the assembly comprising MPHFM fiber 33 on spindle 31 placed in liquid 37 held in container 36 to accomplish the stripping step.

Application 5. Stripping Analyte from an Emulsion

Yet another way the device of FIG. 1 can be used is to place both an aqueous feed sample and an immiscible organic solvent into empty container 36. The contents of container 36 are then agitated by a suitable means known in the art (e.g. a Vortex mixer) to form an emulsion in container 36 and cause extraction of an analyte from the feed liquid portion of the emulsion into the organic solvent portion of the emulsion held in container 36. Then the assembly comprising spindle 3 and lipophilic MPHFM fiber 33 (which contains a stripping solution in its lumen) is placed in the container 36 in order to submerge the MPHFM fiber 33 in the emulsion. Since the lipophilic (e.g. when made of polypropylene) MPHFM fiber 33 is preferentially wet by the organic solvent portion of the emulsion, the organic solvent will adhere to the MPHFM fiber 33 and fill its pores, whereby analyte will be stripped from the organic solvent into the stripping solution contained within the lume of the MPHFM fiber 33.

It is also possible to start with the apparatus already assembled as shown in FIG. 1 and introduce a feed sample and organic solvent (pre-emulsified if desired) into container 36 and stripping solution in MPHFM fiber 33. Thereupon analyte is extracted from feed sample into organic solvent and stripped from the organic solvent (which wets the outer wall of MPHFM fiber 33 into the stripping solution in the lumen of MPHFM fiber 33. Mixing is performed as before to enhance the rate of mass transfer. The procedures of this Application can also be performed with an emulsion of feed sample and organic solvent in the lumen of MPHFM fiber 33 and a stripping solution held as liquid 37 in container 36.

The device shown in FIG. 2 can also be used in any of the foregoing applications in essentially the same manner as the device of FIG. 1. However, the device of FIG. 2 is particularly useful for inserting into a small conduit such as a blood vessel in order to extract an analyte from a fluid (such as blood) flowing in the conduit. For insertion into a blood vessel, supporting body 42 can be a thin wire and the assembly comprising MPHFM fiber and supporting body 42 can then fit conveniently through a catheter into a blood vessel; in the latter case, blood flowing in the blood vessel substitutes for the liquid 45 in container 46.

It is evident that the foregoing device, as depicted in FIG. 1 or FIG. 2, is very versatile regarding the way it can be used to perform forward liquid extraction, or a back extraction (stripping) or both. The device is easy to construct and simple to use. It permits the convenient use of very small volumes, less than 1 ml and even as small as 1 microliter, for feed sample or for solvent or for stripping solution. Use of small volumes of solvents for analytical sample preparation is extremely advantageous to minimize exposure of laboratory personnel to hazardous materials and to lessen the costs of disposal of used-solvent waste. In addition to permitting the use of very small volumes, the single fiber device also permits good control of the liquid volumes and eliminates fluid mal-distribution in multiple fibers, a problem that has plagued the prior art. With good control of liquid volumes, the device can be used to conduct quantitative extraction with known, determined volumes as required in sample preparation by extraction for quantitative analysis of an analyte.

The foregoing single fiber MPHFM devices can also be applied to gas absorption into a liquid of known and controlled volume in the lumen from a gas outside the MPHFM, or from a gas inside the lumen into a liquid of known and controlled volume outside the MPHFM. For example, a liquid held in the lumen can be used to absorb an analyte (e.g. an air pollutant such as $SO_2$) from a gas flowing over the outside of the MPHFM. Similarly, these devices can be applied to stripping a gas from a liquid of known and controlled volume inside the lumen into a gas outside the MPHFM, or from a gas of known and controlled volume outside the MPHFM into a gas in the lumen. In addition, they can be applied to combined, simultaneous gas absorption and stripping, e.g. gas stripping of an analyte from a liquid on one side of the membrane to a gas held in the membrane pores and then absorption from the gas in the pores into another liquid on the other side of the MPHFM. For example, it is possible to strip ammonia from an alkaline aqueous solution contacting one side of a polypropylene MPHFM into air within the pores of the membrane and simultaneously absorb ammonia from the gas in the pores into an acidic aqueous solution in contact with the other side of the membrane.

The process and device for LLE described supra can be operated in several modes, including: a) simultaneous, b) supported liquid membrane, c) sequential, d) with partial evaporation conducted between sequential forward extraction and back-extraction, e) with substantially total evaporation performed between a forward extraction step and a subsequent step to redissolve the solute residue in a product liquid and, f) single-step forward extraction. In addition to these choices of modes, choices must also be made of the sizes of the volumes of the various liquids to be employed. To provide guidance in making choices among the several possible modes of operation, calculations of concentration, $C_p$, of solute in product liquid and of the extent of recovery of solute in product liquid can be made by assuming that equilibrium is attained in the apparatus with an assumed process mode. If one is interested mainly in assaying the solute in the stripping liquid, then one usually would want to maximize the concentration of solute in the stripping liquid to obtain maximum analytical sensitivity; we term this "analytical use" herein. If one is interested in obtaining greatest recovery of the solute, then one may wish to forego obtaining maximum concentration of solute in the stripping liquid, and use larger volumes of stripping liquid to increase solute recovery; we call this type of application "recovery use" herein.

The following mathematical symbols are defined below to develop methods of computing the equilibrium concentration of solute in the product liquid and the equilibrium recovery of solute in the product liquid for the various modes of operation:

$DD_f$ = distribution coefficient for forward extraction; this is also written as DF in computer code notation.

$D_b$ = distribution coefficient for back extraction; this is also written as DB in computer code notation.

Z = fraction of the solvent that is evaporated.

$C_{f1}$ = initial concentration of solute in feed liquid.

$C_{f2}$ = final concentration of solute in feed liquid (after equilibrium is attained).

$C_{s1}$ = initial concentration of solution in solvent liquid ($C_{s1}$ is here assumed to be zero).

$C_{s2}$ = final concentration of solute in solvent liquid (after equilibrium is attained).

$C_{p1}$ = initial concentration of solute in product liquid ($C_{p1}$ is here assumed to be zero).

$C_{p2}$ = final concentration of solute in product liquid (after attainment of equilibrium).

F, S, P = respective volumes of feed liquid, solvent liquid and stripping liquid.

CR = concentration ratio, ratio of solute concentration in the product liquid to that in the feed liquid.

RR = recovery ratio, ratio of the amount of solute in the product liquid to that in the feed liquid.

For Simultaneous Operation

A mass balance which equates the amount of solute initially in the feed liquid ($FC_{f1}$) with the amounts in all three phases in simultaneous equilibrium with each other is:

$$FC_{f1} = FC_{f2} + SC_{s2} + PC_{p2} \quad (2)$$

The distribution coefficients:

$$D_f = C_{s2}/C_{f2} \quad (3)$$

and $$D_d = C_{s2}/C_{p2} \quad (4)$$

are then used to eliminate $C_{f2}$ and $C_{s2}$ from equation (2) with the following result for product-to-feed concentration ratio, CR:

$$CR = C_{p2}/C_{f1} = 1/(D_b/D_f + (SD_b)/F + P/F) \quad (5)$$

The foregoing equation gives the ratio of equilibrium solute concentration in the product stripping liquid to that initially in the feed liquid. This ratio would usually be maximized for "analytical use". The corresponding solute-recovery ratio, RR, for simultaneous-mode operation, which would ordinarily be maximized for "recovery use", is:

$$RR = (PC_{p2})/(FC_{f1}) = 1/((FD_b)/(PD_f) + (SD_b)/P + 1) \quad (6)$$

Inspection of equation (5) indicates that maximum CR is obtained with: $D_b$, S and P as small as possible and $D_f$ and F as large as possible. Inspection of equation (6) indicates that maximum RR is obtained with $D_b$ F and S as small as possible and with P and $D_f$ as large as possible.

Supported Liquid Membrane Operation

This is a special case of simultaneous operation to which the same equations (5) and (6) apply. However, the volume of solvent, S, is now smaller and corresponds to the volume of the pores $V_p$ (or VP in computer code notation) in the MPHFM's. This value of $V_p$ can be estimated as the volume of the fiber walls multiplied by their fractional porosity. The value of $V_p$ can then be used in place of S in equation (5) and (6). Examination of equations (5) and (6) shows that lowered values of S, such as are possible with supported liquid membranes, lead to higher values of the concentration ratio, CR, and the recovery ratio, RR. However, supported solvent membranes can be unstable and the solvent sometimes can easily flow or evaporate out of the pores during operation.

For Sequential Operation Without Evaporation

The mass balance for forward extraction is:

$$FC_{f1} = FC_{fs} + SC_{s2} \quad (7)$$

The back-extraction is accomplished with pure stripping liquid, for which $C_{p1} = 0$. The solvent composition is $C_{s2}$ after forward but before back-extraction, and $C_{ss3}$ after back-extraction. The mass balance for back-extraction is:

$$S[C_{s2} - C_{s3}] = PC_{p2} \quad (8)$$

The foregoing equations (7) and (8) can be algebraically manipulated together with the distribution coefficient expressions:

$$D_f = C_{s2}/C_{f2} \quad (9)$$

and $$D_b = C_{s3}/C_{p2} \quad (10)$$

to eliminate $C_{f2}$, $C_{s3}$ and $C_{s2}$ to give:

$$CR = C_{p2}/C_{f1} = 1/\{P/(D_f S) + P/F + D_b/D_f + (D_b S)/F\} \quad (11)$$

$$RR = (PC_{p2})/(FC_{f1}) = 1/\{F/(D_f S) + 1 + (D_b F)/(D_f P) + (D_b S)/P\} \quad (12)$$

Equation (11) states that CR or $C_{p2}$ is increased by increasing $D_f$ and F and decreasing P and $D_b$. Equation (12) indicates that RR is increased by increasing $D_f$ and P and decreasing F and $D_b$. There is an optimum value of S, $S_{opt} = [PF/(D_b D_f)]^{\frac{1}{2}}$ which maximizes both CR or RR. This expression for $S_{opt}$ can be obtained by taking the partial derivative with respect to S of the right-hand side of either equation (11) or (12), setting the derivative equal to zero, and solving the resulting equation for $S_{opt}$.

Sequential Contacting With Evaporation

If the solvent liquid, originally of volume S during the forward extraction, is evaporated by a fraction Z after forward extraction, then the solvent volume after evaporation and during the back extraction process is $S(1-Z)$. The mass balance for back extraction is then as follows:

$$SC_{s2} = (1-Z)SC_{s3} + PC_{p2} \quad (13)$$

When this equation is solved as before with the mass balance equation (7) for the forward extraction and the two equations (9) and (10) defining the distribution coefficients, the results for CR and RR are:

$$CR = C_{p2}/C_{f1} = 1/\{P/(D_f S) + P/F + ((1-Z)D_b)/D_f + ((1-Z)D_b S)/F\} \quad (14) \text{ and}$$

$$RR = (PC_{p2})/(FC_{f1}) = 1/\{F/(D_f S) + 1 + ((1-Z)D_b F)/(D_f P) + ((1-Z)D_b S)/P\} \quad (15)$$

By inspection, maximum Cr will be obtained for P as small as possible, F and large as possible, and Z as close to 1.0 as possible. In contrast, maximum RR will be obtained with P as large as possible, F as small as possible and Z as close to 1.0 as possible. Use of the derivative calculus as before indicates that once F, P and Z are fixed, then the optimum value of S to maximize either RR or CR is:

$$S_{opt} = [(PF)/((1-Z)D_b D_f)]^{\frac{1}{2}} \quad (16)$$

Equation (16) is obtained by taking the partial derivative with respect to S of either equation (14) or (15), setting the derivative equal to zero, and solving the resulting equation for $S = S_{opt}$. This expression [equation (16)] for $S_{opt}$ is applicable also to the sequential mode without evaporation by setting $Z=0$. Because the starting volume of solvent may be set by the physical dimensions of the apparatus, the last optimum criterion of equation (16) can be restated, for a given value of S, as:

$$(P \cdot F)_{opt} = S^2(1-Z)D_b D_f \quad (17)$$

Thus for maximum CR, P should be as small as possible and F as large as possible and their product should be given by equation (17). Similarly, for maximum RR, P should be as large as possible and F as small as possible and their product should also be given by equation (17). In case equations (16) or (17) are far from being satisfied by the values of P and F selected and the value of S corresponding tot he apparatus, it means that there is a mismatch between feed-liquid volume F, product-liquid volume, P and the solvent volume of the apparatus.

Sequential Operation with Complete Evaporation of the Solvent

Equation (14) for CR and equation (15) for RR also apply to the total-evaporation case with $Z=1$ and P = the volume of product liquid that is used to dissolve the solute residue after total evaporation of the solvent. Equation (16) is also applicable and predicts that in the present case of substantially complete evaporation, maximum CR and maximum RR are obtained by making the original volume of solvent liquid as large as possible.

Single-Step Forward Extraction

Equation (7) for the forward-extraction step can be combined with the definition of $D_f$ in equation (3) to eliminate $C_{f1}$ thereby giving:

$$CR = C_{s2}/C_{f1} = 1/[1/D_f + S/F] \quad (18)$$

$$RR = SC_{s2}/FC_{f1} = 1/[F/(SD_f) + 1] \quad (19)$$

Here CR and RR have somewhat different algebraic forms because the product liquid is the solvent liquid in the case of single-step forward extraction. These equations show that CR is increased by increasing F and decreasing S, whereas RR is increased by increasing S and decreasing F. The value of CR or $C_{s2}$ can be further enhanced by evaporation of the solvent after extraction; for example, 50% evaporation can increase $C_{s2}$ by a factor of 2 and 90% evaporation by a factor of ten.

The various foregoing equations for CR and RR may be used with any consistent units for the volume terms F, S and P. It is noted that CR, RR, $D_f$ and $D_b$ are dimensionless as defined herein.

The foregoing equations for CR and RR are developed from mass balance and equilibrium assumptions. As such, they predict the values of CR and RR that would result if equilibrium between the phases were attained. Although considerable contact time may be required to attain equilibrium, the equilibrium-based equations predict the best values of CR and RR that can be realized under equilibrium conditions for a given operational mode and with a given set of distribution coefficients and liquid volumes. Thus these equations permit equilibrium performance by the individual modes of operation to be compared for a given set of distribution coefficients and liquid volumes. Alternatively, the equations for a given mode of operation can be used to indicate how to choose the individual liquid volumes to maximize CR and RR for that particular mode, and with given distribution coefficients. Examination of the equations for CR and RR shows that, for a given set of distribution coefficients and liquid volumes, CR and RR will always be smaller for non-evaporative, sequential operation [equations (11) and (12)] than for simultaneous operation [equations (5) and (6)], because there is an additional term in the denominator of each expression for sequential operation. Sequential operation with evaporation, however, can deliver larger values of CR and RR if the values of Z are made sufficiently close to unit, i.e., if sufficient evaporation of solvent liquid is performed.

The foregoing equations permit a set of rules to be stated regarding how to adjust volumes to increase values of CR or RR. These rules are: (1) For any mode of operation CR is increased by increasing F and decreasing P (or decreasing S in single-step forward extraction where the solvent solution is the product solution). (2) For any mode of operation, RR is increased by decreasing F and increasing P (or increasing S in single-step forward extraction where the solvent solution is the product solution). (3) For simultaneous operation, decreasing S causes CR and RR to increase. (4) To maximize both CR and RR in sequential operation with given values of P and F, there is an optimum value of S equal to $[(PF)/((1-Z)D_bD_f)]^{\frac{1}{2}}$, where Z=fraction evaporated, Z=0 corresponds to sequential operation with no evaporation, and Z=1 corresponds to complete evaporation of solvent after forward extraction, with the total-evaporation step followed by dissolving solute residue in product liquid of volume P. Note that the mathematically predicted optimum value of the solvent volume, $S_{opt}$, may be physically impractical, e.g., it may be too small to submerge the desired number of fibers in a particular device. With total evaporation [Z=1], equation (16) predicts an infinite value of $S_{opt}$, and this means the initial value of S should be chosen as large as possible, i.e. as large as the size of the apparatus permits.

In order to choose the best operational mode for the LLE process with an apparatus such as shown in FIG. 1 of the parent application Ser. No. 07/411,683, this invention provides a data-processing methodology based on the foregoing equations that can compute and output the values of CR and RR for each operational mode, when a given set of liquid volumes and distribution coefficients are supplied. The data processing methodology can also output rules and advice on how best to select the liquid volumes to maximize CR and RR for each mode. Thus the data processing methodology also provides the user with the ability to choose and change the input values of liquid volumes to explore how changing the amounts of the liquid volumes can affect the values of CR and RR for each mode. FIG. 2 of the parent application Ser. No. 07/411,683 depicts a schematic flow chart of a data processing methodology provided by the present invention. Referring to FIG. 2 of the parent application Ser. No. 07/411,683, step 21 is an operation is which the required parameters (e.g., DF, DB, F, P, S, VP) are supplied to the system. In step 22, the values of RR and CR are computed for each operational mode under consideration, using mass balance equations and definitions of DF and DB as, for example, by using the equations developed supra. Values of optimum solvent volumes for sequential operation are also computed in step 22; various extents of solvent operation can be included in the calculations, as desired. Step 23 outputs (i.e., supplies) the values computed in step 22, e.g., by printing or by displaying the values on a screen. Test 24 queries the user whether the volume selection rules should be outputted and, if so desired, these rules are outputted by step 25. Test 29 queries the reader whether additional calculations are to be made and transfers system control according to the answer to the query.

Table 1 is an embodiment of the data processing methodology shown in the schematic flow diagram of FIG. 2 of the parent application Ser. No. 07/411,683. Table 1 shows a computer program written in the BASIC computer language using the parameter symbols defined herein and standard BASIC statements. The application and use of the BASIC computer language can be found described in the textbook, *BASIC: A Programmed Text* by S. Hirsch, John Wiley and Sons, Inc. (1975).

TABLE 1

| | BASIC COMPUTER PROGRAM LISTING |
|---|---|
| 100 | PRINT "enter value of forward extraction distribution coefficient" |
| 105 | INPUT DF |
| 110 | PRINT "enter value of back-extraction distribution coefficient" |
| 115 | INPUT DB |
| 120 | PRINT "enter value of feed liquid volume" |
| 125 | INPUT F |
| 130 | PRINT "enter value of stripping-liquid volume" |
| 135 | INPUT P |
| 140 | PRINT "enter value of solvent volume" |
| 145 | INPUT S |
| 150 | PRINT "enter value of membrane pore volume" |
| 155 | INPUT VP |

TABLE 1-continued
BASIC COMPUTER PROGRAM LISTING

```
160  CRSIM =1/(DB/DF+S*DB/F+P/F)
165  RRSIM=1/(F*DB/(P*DF)+S*DB/P+1)
170  CRSUP=1/(DB/DF+VP*DB/F+P/F)
175  RRSUP=1/(F*DB/(P*DF)+VP*DB/P+1)
176  CRSS=1/(1/DF+S/F)
177  RRSS=1/(F/(F*DF)+1)
180  CRSEQ=1/(P/(DF*S)+P/F+DB/DF+DB*S/F)
185  RRSEQ=1/(F/(DF*S)+1+DB*F/(DF*P)+DB*S/P)
190  SOPT=SQR(P*F/(DB*DF))
195  Z=1
200  FOR I=1 TO 4
205  CR(I)=1/(P/(DF*S)+P/F+(1−Z)*DB/DF+(1−Z)*DB*S-
     /F)
206  RR(I)=1/(F/(DF*S)+1+(1−Z)*DB*F/(DF*P)+(1−Z)*D-
     B*S/P)
207  SOPT(I)=SQR(P*F/((1−Z)*DB*DF))
210  Z=Z−.25
215  NEXT I
220  PRINT "VALUES OF CONCENTRATION RATIO:"
225  PRINT "for simultaneous mode          ";CRSIM
230  PRINT "for supported solvent membrane ";CRSUP
231  PRINT "for single-step forward extr.  ";CRSS
235  PRINT "for sequential mode, no evap   ";CRSEQ
240  PRINT "for sequential with 100% evap  ";CR(1)
245  PRINT "for sequential with 75% evap   ";CR(2)
250  PRINT "for sequential with 50% evap   ";CR(3)
251  PRINT "for sequential with 25% evap   ";CR(4)
255  PRINT "VALUES OF RECOVERY RATIO:"
260  PRINT "for simultaneous mode          ";RRSIM
265  PRINT "for supported solvent membrane ";RRSUP
266  PRINT "for single-step forward extr.  ";RRSS
270  PRINT "for sequential mode, no evap   ";RRSEQ
275  PRINT "for sequential with 100% evap  ";RR(1)
276  PRINT "for sequential with 25% evap   ";RR(2)
280  PRINT "for sequential with 50% evap   ";RR(3)
285  PRINT "for sequential with 25% evap   ";RR(4)
286  PRINT "Parameters used are
     S=";S;"VP=";VP;"F=";F;"P=";P;"DF=";DF;"DB=";DB
287  PRINT "enter cont to continue calculations"
288  STOP
290  PRINT "OPTIMUM SOLVENT VOLUMES FOR
     SEQUENTIAL MODES:"
295  PRINT "with 100% evap   ";SOPT(1)
300  PRINT "with 75 evap     ";SOPT(2)
305  PRINT "with 50% evap    ";SOPT(3)
306  PRINT "with 25% evap    ";SOPT(4)
310  PRINT "with 0% evap     ";SOPT
311  PRINT "optimum solvent volume =
     SQRT[P*F/((1−Z)*DF*DB)]"
315  PRINT "Parameters used are
     S";S;"VP";VP;"F";F;"P";P;"DF";DF;"DB";DB
316  PRINT "PRINT OUT GENERAL RULES?
     ENTER 1 FOR YES, 0 FOR NO."
317  INPUT ANS
318  IF ANS=0 THEN 324
319  PRINT "For all modes of operation, the concentration ratio,
     CR, is increased by making F as large as possible and P
     as small as possible (P refers to solvent in the case
     of single-step forward extraction)."
320  PRINT "For all modes of operation, the recovery ratio,
     RR, is increased by making F as small as possible and
     P as large as possible (P refers to solvent in the
     case of single-step, forward extraction)."
321  PRINT "For simultaneous operation, decreasing
     solvent volume, S or VP, increases both CR and RR."
322  PRINT "For sequential operation the optimum
     solvent volume depends on the values of both F and P
     and is given by SQRT[P*F/((1−Z)*DF*DB)]"
324  PRINT "Do another calculation? Enter 1 for yes, 0 for no."
325  INPUT ANS
330  IF ANS=1 THEN 100
340  END
```

In operation, the BASIC object program of Table 1 is input into the random access memory (RAM) of a computer under the control of a BASIC software program already present in the RAM. The BASIC software program is generally loaded into the RAM from an input device such as a floppy-disc drive, a hard-disk drive or magnetic tape. The object program can be similarly input or it can be entered via a keyboard console. The results from the operation of the object computer program can be outputted to a printer, a CRT screen, a liquid crystal screen, magnetic or optical media or to another output device. An important embodiment of the present invention is a device as in FIG. 1 of the parent application Ser. No. 07/611,683 in combination with a digital computer, a source program such as a BASIC software source code, an object program such as a BASIC object code as in Table 1, and suitable input and output means in conjunction with the RAM of said computer. Said RAM can contain the object and source programs or receive same as input from an input device.

EXAMPLES

The Examples which follow relate to simultaneous extraction and stripping of the drug theophylline.

EXAMPLE 1

This Example shows the effect of time. A device as depicted in FIG. 1 was used with a spindle about 2 cm high and about 7 mm in diameter with 100 cm of a single Celgard MPHFM fiber (400 micrometer i.d.) wound on the spindle. In the lumen of the MPHFM fiber was placed 100 microliters of an aqueous solution containing 0.5 mg/ml of theophylline in $K_2HPO_4$/NaCl buffer as the feed sample. The MPHFM pores were filled with a solvent mixture of chloroform and isopropanol in volume ratio 19:1; the assembly comprising MPHFM and spindle was then placed in 2 ml of an aqueous stripping solution containing 0.1 N NaOH and 10% (v/v) isopropanol held in a small cylindrical container. The spindle was rotated relative to the container (held stationary) at about 150 rpm. The stripping solution was then analyzed for theophylline by uv spectrophotometry. This experiment was repeated numerous times, each time for a different period of simultaneous extraction and stripping with the results as given below.

| Duration of Experiment, min | Fraction of Theophylline in Feed Sample Transferred to Stripping Solution, % |
|---|---|
| 1 | 52 |
| 2 | 71 |
| 5 | 82 |
| 10 | 87 |
| 15 | 89 |
| 30 | 90 |
| 60 | 94 |

EXAMPLE 2

This Example shows the effect of different starting concentrations of theophylline analyte. Experiments were conducted as in Example 1 except that the volume of stripping solution was 300 microliters and the duration of the experiment was always 60 min. Different starting concentrations of theophylline in the feed sample solution (100 microliters) in the lumen were used in each experiment with the following results:

| Starting Conc. of Theophylline in Lumen, microgram/ml | Fraction of Theophylline in Feed Sample Transferred to Stripping Solution, % |
|---|---|
| 0.78 | 80 |
| 1.56 | 57 |

-continued

| Starting Conc. of Theophylline in Lumen. microgram/ml | Fraction of Theophylline in Feed Sample Transferred to Stripping Solution, % |
|---|---|
| 3.12 | 68 |
| 6.25 | 71 |

The fraction recovered in Example 2 is less than in Example 1 because of the smaller volume of stripping solution employed in Example 2.

EXAMPLE 3

This Example shows the effects of different starting concentrations of theophylline analyte, but with a larger volume of stripping solution than in Example 2. Experiments were conducted exactly as in Example 2, except that the volume of stripping solution was 2000 microliters, with the following results:

| Starting Conc. of Theophylline in Lumen. microgram/ml | Fraction of Theophylline in Feed Sample Transferred to Strippinh Solution. % |
|---|---|
| 62.5 | 83 |
| 125 | 91 |
| 250 | 88 |
| 500 | 94 |

EXAMPLE 4

This Example shows the effect of mixing by rotating the spindle. Experiments were conducted exactly as in Example 1, except that the volume of stripping solution was 3 ml and the time of each experiment was 5 minutes. One experiment was conducted with mixing by rotating the spindle as in Example 1, the other with no mixing (no rotation). The results are:

| | Fraction of Theophylline in Feed Sample Transferred to Stripping Solution, % |
|---|---|
| With mixing: | 81.2 |
| Without mixing: | 68 |

To those skilled in the art to which this invention relates, many changes in construction or materials and widely different embodiments and applications of the invention will suggest themselves without departing from the spirit and scope of the invention. For example, in this invention fluids may be fed continuously or processed batchwise for purification by mass transfer. Also, mass transfer can be accomplished using supercritical fluids or slurries or aerosols in this invention, in addition to liquids and gases. Similarly, various shapes, sizes and configurations can be used for the apparatus and methods of the invention. In this invention the wetting characteristics of a MPHFM can be changed by any one of several treatments known in the art, for example oxidizing the outer surface of a polypropylene MPHFM in order to render the outer surface hydrophilic while the inner surface remains hydrophobic. Alternatively, both the outer and inner surfaces of a MPHFM could be rendered hydrophobic while the interiors of the pores remainded hydrophobic. In any event, the disclosures and the descriptions herein are purely illustrative and are not intended to be in any sense limiting.

We claim:

1. A device constructed and arranged for conducting liquid extraction of an analyte from a sample liquid into another liquid that is substantially immiscible with said sample liquid, followed by analytical assay of said analyte in one of the liquids comprising:
   (a) a microporous hollow-fiber membrane means,
   (b) a supporting body on which is mounted said microporous hollow-fiber membrane means,
   (c) means for introducing one of said liquids into the lumen of said microporous, hollow-fiber membrane means, and
   (d) means for analytical assay of said analyte in one of said liquids,
   wherein mass transfer of said analyte can occur between said liquids when said device containing one of said liquids in said lumen is placed in the other of said liquids, and said analyte can be assayed in one of said liquids.

2. The device according to claim 1 additionally comprising a container suitable for holding one of said liquids and into which container fits said supporting body with said microporous membrane means mounted thereon.

3. The device according to claim 2 wherein the surface of said supporting body is a mass-transfer enhancing surface.

4. The device according to claim 2 wherein the lumen volume of said microporous hollow fiber membrane means is in the range of several microliters to several milliliters.

5. The device according to claim 2 wherein said microporous hollow fiber membrane means comprises a single fiber.

6. The device according to claim 5 wherein said microporous hollow fiber membrane means is wound around said supporting body.

7. The device according to claim 6 wherein said supporting body and said container are of circular cylindrical shape.

8. The device according to claim 7 wherein the lumen volume of said microporous hollow fiber membrane means is in the range of several microliters to several milliliters.

9. The device according to claim 7 additionally comprising means for mixing at least one of said liquids in said device.

10. The device according to claim 9 additionally comprising means for introducing one of said liquids into said container.

11. The device according to claim 10 wherein the lumen volume of said microporous hollow fiber membrane means is in the range of several microliters to several milliliters.

12. The device according to claim 9 wherein said means for mixing comprises means for causing relative movement between said container and said supporting body.

13. The device according to claim 12 wherein the lumen volume of said microporous hollow fiber membrane means is in the range of several microliters to several milliliters.

14. The device according to claim 9 wherein the lumen volume of said microporous hollow fiber membrane means is in the range of several microliters to several milliliters.

15. A method of causing mass transfer of an analyte between two fluids employing the device of claim 1, comprising:

(a) placing one of the fluids in said lumen of said device,
(b) placing said device into the other fluid,
(c) mixing at least one of said fluids, and
(d) assaying said analyte in at least one of said fluids.

16. The method according to claim 15 wherein said microporous hollow fiber membrane means comprises a single fiber.

17. The method according to claim 15 wherein mixing of said fluid external to said lumen is caused by holding said device submerged in said external fluid in such a way as to bring about relative motion of said external fluid relative to said device.

18. The method according to claim 15 wherein each of said fluids is a liquid.

19. The method according to claim 15 wherein at least one of said fluids is a liquid and at least one other of said fluids is a gas.

20. The device according to claim 1 wherein the lumen volume of said microporous hollow fiber membrane means is in the range of several microliters to several milliliters.

21. A device constructed and arranged for conducting liquid extraction of an analyte from a sample liquid into another liquid that is substantially immiscible with said sample liquid, comprising:
(a) a microporous hollow-fiber membrane means,
(b) a supporting body on which is mounted said microporous hollow-fiber membrane means comprising a single fiber wound around said supporting body,
(c) means for introducing one of the liquids into the lumen of said microporous, hollow-fiber membrane means,
(d) container means suitable for holding one of said liquids and into which container fits said supporting body with said microporous membrane means mounted thereon, and
(e) means for mixing at least one of said liquids in said device that causes relative movement between said container and said supporting body,
wherein mass transfer of said analyte can occur between said liquids when said device containing one of said liquids in said lumen is placed in the other of said liquids.

22. The device according to claim 21 wherein the volume of said lumen of said microporous hollow fiber membrane means is in the range of several microliters to several milliliters.

* * * * *